July 5, 1966 E. S. BOERNER Plant Pat. 2,652
ROSE PLANT
Filed Aug. 17, 1965
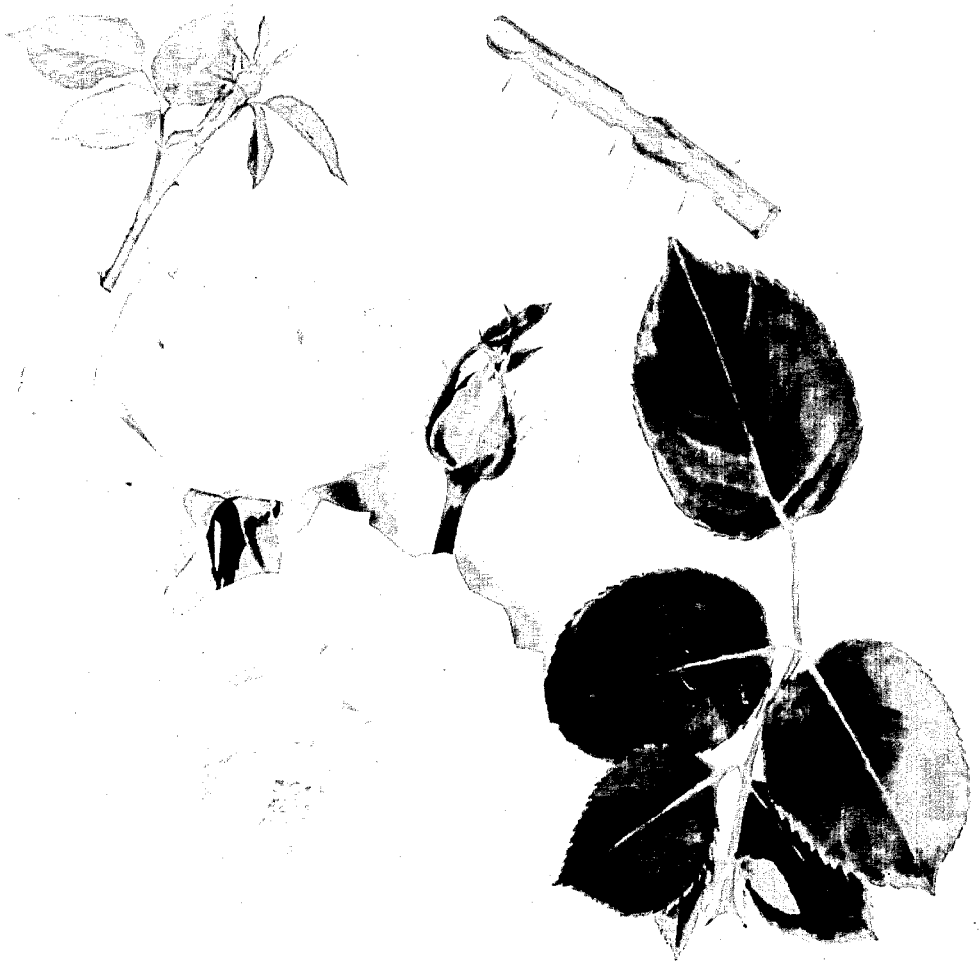
Inventor.
E. S. Boerner
By: Robb & Robb
Attorneys.

United States Patent Office

Plant Pat. 2,652
Patented July 5, 1966

2,652
ROSE PLANT

Eugene S. Boerner, Newark, N.Y., assignor to Jackson & Perkins Company, Newark, N.Y., a corporation of New York Filed Aug. 17, 1965, Ser. No. 480,535
1 Claim. (Cl. Plt.—11)

The present invention relates to a new and distinct variety of rose plant of the hybrid tea class, which was originated by me by crossing an unnamed and unpatented seedling of the rose variety known as "Diamond Jubilee" (Plant Patent No. 824) with another unnamed and unpatented seedling derived from a cross of the variety "Goldilocks" (Plant Patent No. 672) × "Orange Nassau" (Plant Patent No. 350).

The primary objective of this breeding was to produce a new and improved rose variety which bears long-lasting and large flowers in a highly colored form of the flowers of the parent variety "Diamond Jubilee." This objective was fully achieved, along with other desirable improvements, as evidenced by the following unique combination of characteristics which are outstanding in the new variety and which distinguish it from its parents, as well as from all other varieties of which I am aware:

(1) Large size foiliage;
(2) Very large bloom size;
(3) Good keeping qualities of the flowers; and
(4) A distinctive and attractive general color tonality of the flowers, beginning in the bud stage as Light Buff, with the outer edges of the petals overcast with La France Pink, and finishing in the open flower stage as Pale Ochraceous-Buff, overcast with Shell Pink, and with the lower half of the petals lightly overcast with Maize Yellow.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed and unpatented seedling of "Diamond Jubilee."
*Pollen parent.*—An unnamed and unpatented seedling of "Goldilocks" × "Orange Nassau."

Classification:
*Botanic.*—Hybrid tea.
*Commercial.*—Hybrid tea.

*Flower*

(Observations made from specimens grown outdoors at Newark, New York, in the early morning during the latter part of the month of August.)

Blooming Habit: Recurrent—continuous.

Bud:
*Size.*—Large.
*Form.*—Ovoid; is not affected by wet or hot weather.
*Color.*—When sepals first divide—Antimony Yellow, Plate 15. When petals begin to unfurl—Pale Ochraceous-Salmon, Plate 15, lightly overcast with Pale Vinaceous Pink, Plate 28. When half blown: Inside of petals—Light Buff, Plate 15, with the outer edges overcast with La France Pink, Plate 1; reverse of petals—Pale Ochraceous Buff, Plate 15, with the outer edges overcast with Shell Pink, Plate 14 and the lower half of the petals overcast lightly with Buff-Yellow, Plate 4.
*Sepals.*—Branched; curl back when petals begin to unfurl. Color: Inside—Light Turtle Green, Plate 32; outside—Biscay Green, Plate 17.
*Calyx.*—Color—Biscay Green, Plate 17. Shape—funnel. Size — large. Aspect — smooth. Odor when rubbed—none.
*Peduncle.* — Length — long. Aspect — rough. Strength—erect; heavy. Color—Oil green, Plate 5, overcast lightly with Brick Red, Plate 13.
*Opening.*—Opens up well; is not affected by adverse conditions.
*Size.*—Very large. Average size when fully expanded—from 6 to 6½ inches.

Bloom:
*Borne.*—Both singly and several together.
*Stems.*—Medium length; strong.
*Form (when first open).*—Cupped, then flattens as it finishes. Permanence—retains its form to the end and flattens, with outer petals curling back as it finishes.
*Petalage.*—Double (full but open center). Number of petals under normal conditions—from 50 to 55.
*Color.*—Center of flower—Pale Ochraceous-Salmon, Plate 15, lightly overcast with Shrimp Pink, Plate 1. Outer petals—Light Buff, Plate 15, with outer edges of petals very lightly overcast with Shell Pink, Plate 28. Base of petals—Mustard Yellow, Plate 16. Inside of petals—Pale Ochraceous-Buff, Plate 15, overcast with Shell Pink, Plate 28, with lower half of petals lightly overcast with Maize Yellow, Plate 4. Reverse of petals—Cartridge Buff, Plate 30, very lightly overcast with Pale Pinkish Buff, Plate 29. General tonality from a distance—Pale Ochraceous-Salmon, Plate 15, very lightly overcast with Shrimp Pink, Plate 1.
*Discoloration.*—General tonality at end of first day Pale Ochraceous-Salmon, Plate 15, lightly overcast with Shrimp Pink, Plate 1. Second day—Pale Ochraceous-Buff, Plate 15, overcast with Shell Pink, Plate 28, with lower half of petals lightly overcast with Maize Yellow, Plate 4. Third day—Pale Ochraceous-Buff, Plate 15, overcast with Shell Pink, Plate 28, with lower half of petals lightly overcast with Maize Yellow, Plate 4.

Petals:
*Texture.*—Thick; is not affected by wet or hot weather.
*Appearance.*—Inside—satiny. Outside—shiny.
*Form.*—Oval, slightly notched.
*Arrangement.* — Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles.
Stamens, filaments (threads): Medium length. Color—Eugenia Red, Plate 13.
Pollen: Color—Pale Yellow-Orange, Plate 3.
Styles: Bunched; uneven length; medium length; thin.
Stigmas: Color—Buff Yellow, Plate 4.
Ovaries: All enclosed in calyx.
Hips: None.
Seeds: None.

*Plant*

Form: Bush.
Growth: Vigorous; upright.
Foliage: Compound of 3 to leaflets.
*Size.*—Large.
*Quantity.*—Normal.
*Color.*—New foliage: Upper side—Olive Lake, Plate 16, lightly overcast with English Red, Plate 2; under side—Honey Yellow, Plate 30, very lightly overcast with Cress Green, Plate 31. Old foliage: Upper side—Cress Green, Plate 31; under side—Jade Green, Plate 31.
*Shape.*—Oval pointed.
*Texture.*—Upper side—glossy. Under side—smooth.
*Ribs and veins.*—Ordinary.
*Edge.*—Serrated (saw toothed).
*Serration.*—Both double and single; small.
*Leaf stem.*—Color—Rainette Green, Plate 31. Under side—prickly.
*Stipules.*—Medium length; smooth.
Wood:
*New wood.*—Color—Oil Green, Plate 5, lightly overcast with Vinaceous Cinnamon, Plate 29. Bark—smooth.
*Old wood.*—Color—Parrot Green, Plate 6. Bark—smooth.
Thorns:
*Thorns.*—Quantity: On main stalks from base—ordinary; on laterals from stalk — ordinary. Form—narrow base; medium length; hooked downward. Color (when young)—Acajou Red, Plate 13. Position—Irregular.
*Prickles.*—Quantity: On main stalks—none; on laterals—none.
*Short needles.*—On main stalks—none; on laterals—none.

I claim:

A new and distinct variety of rose plant of the hybrid tea class, substantially as herein shown and described, characterized particularly as to novelty by the unique combination of large size foliage, very large bloom size, good keeping qualities of the flowers, and a distinctive and attractive general color tonality of the flowers, beginning in the bud stage as Light Buff, with the outer edges of the petals overcast with La France Pink, and finishing in the open flower stage as Pale Ochraceous-Buff, overcast with Shell Pink, and with the lower half of the petals lightly overcast with Maize Yellow.

No references cited.

ABRAHAM G. STONE, *Primary Examiner.*

R. E. BAGWILL, *Assistant Examiner.*